United States Patent
Woo et al.

(10) Patent No.: US 7,601,391 B2
(45) Date of Patent: Oct. 13, 2009

(54) METHOD OF PREPARING SINGLE NANOPARTICLE CONTAINING ORGANIC-INORGANIC COMPOSITE MATERIAL

(75) Inventors: Kyoungja Woo, Seoul (KR); Dong Hyun Koo, Jeollabuk-do (KR)

(73) Assignee: Korea Institute of Science & Technology, Seoul (KR)

( * ) Notice: Subject to any disclaimer, the term of this patent is extended or adjusted under 35 U.S.C. 154(b) by 224 days.

(21) Appl. No.: 11/642,772

(22) Filed: Dec. 19, 2006

(65) Prior Publication Data

US 2008/0044657 A1 Feb. 21, 2008

(30) Foreign Application Priority Data

Aug. 21, 2006 (KR) .................. 10-2006-0078757

(51) Int. Cl.
*B05D 7/00* (2006.01)
*B06B 1/00* (2006.01)
*B32B 5/16* (2006.01)
(52) U.S. Cl. .................. 427/215; 427/220; 427/600; 977/827; 977/830
(58) Field of Classification Search .............. 427/215, 427/220, 600; 977/827, 830
See application file for complete search history.

(56) References Cited

U.S. PATENT DOCUMENTS 6,319,426 B1 * 11/2001 Bawendi et al. ....... 252/301.4 R
6,881,490 B2 * 4/2005 Kambe et al. ............... 428/447
7,041,371 B2 5/2006 Ogura et al.

OTHER PUBLICATIONS

Warren C. W. chan, et al., "Quantum Dot Bioconjugates for Ultrasensitive Nonisotopic Detection", Science, vol. 281, Sep. 25, 1998, p. 2016-p. 2018.
Wen Jiang, et al., "Design and Characterization of Lysine Cross-Linked Mercapto-Acid Biocompatible Quantum Dots", Chem. Mater., vol. 18, No. 4, Jan. 21, 2006, p. 872-p. 878.
Koo, Donghun; Woo Koungja., Synthesis of Amine-Terminated CdS/CdS Core/Shell Nanoparticle and its Bioconjugation To Carboxyl Activated Poly(ethylene glycol). Abstract. Jul. 2006 in Korea Association for Particle and Aerosol Research.

* cited by examiner

*Primary Examiner*—H. (Holly) T Le
(74) *Attorney, Agent, or Firm*—Anthony M. Insogna; Jaime D. Choi; Jones Day

(57) ABSTRACT

There is provided an organic-inorganic composite material containing a single nanoparticle therein, which is prepared by individually dispersing hydrophilic inorganic nanoparticles having a uniform particle size and conjugating biodegradable polymers to the surface of the nanoparticle, and a method of preparing the same. More particularly, the preparation method of the present invention comprises the following steps: 1) preparing hydrophilic nanoparticles by conjugating organic substances having a thiol group and a hydrophilic amine group to the surface of a core or a core/shell inorganic nanoparticle protected with a surfactant through a metal-thiolate (M-S) bond between them; 2) adjusting the concentration of the hydrophilic nanoparticles prepared in step 1) to $2 \times 10^{-6}$ M or less and treating them in a sonication bath to prepare individually dispersed nanoparticles in the form of a single particle; and 3) conjugating biopolymers to the nanoparticle individually dispersed in step 2) through the formation of an amide bond between them under treatment in a sonication bath. The organic-inorganic composite material of the present invention exhibits high efficient photoluminescence and photostability as well as excellent chemical stability, dispersibility in water, biocompatibility and targetibility. Thus, it can be effectively used as a raw material for bioimaging or film coating.

15 Claims, 7 Drawing Sheets

METHOD OF PREPARING SINGLE NANOPARTICLE CONTAINING ORGANIC-INORGANIC COMPOSITE MATERIAL

FIELD OF THE INVENTION

The present invention relates to an organic-inorganic composite material containing a single nanoparticle therein, which is applicable for bio-imaging and prepared by individually dispersing hydrophilic inorganic nanoparticles having a uniform particle size and conjugating biodegradable polymers to the surface of the single nanoparticle. The present invention further relates to a method of preparing the above organic-inorganic composite material.

BACKGROUND OF THE INVENTION

Since the establishment of a method for synthesizing hydrophobic inorganic nanoparticles having a uniform particle size in an organic solvent containing a surfactant through a chemical process, extensive researches and studies are currently underway for practical applications. Among them, organic-inorganic composite materials, wherein a single inorganic nanoparticle exists at the center thereof and the surface of the nanoparticle is surrounded with polymers, have a wide range of application. This is because they can be effectively used as raw materials for fabrication of an organic-inorganic composite film and coating of substrate. They can also be used as raw materials for bioimaging. Thus, most of the researches have been focused on the practicalization of organic-inorganic composite materials.

Initially, a method of preparing hydrophobic or hydrophilic organic-inorganic composite materials by coating hydrophobic inorganic nanoparticles with polymers having a similar property to the nanoparticle surface or amphiphilic polymers via physical interaction was proposed. However, since the single organic-inorganic composite materials prepared by said method contain multiple inorganic nanoparticles inside, several problems occurred such as low quantum efficiency, size polydispersity and poor conversion yield. Since the adsorption of the polymer onto the nanoparticle is conducted by surrounding multiple inorganic nanoparticles with a single long polymer chain, such problems were regarded as being unavoidable. Thus, various methods were developed to overcome such problems, although they still suffered from poor conversion yield and inclusion of multiple inorganic nanoparticles inside a single composite. Accordingly, many attempts were made to develop a method of preparing an organic-inorganic composite material containing only a single inorganic nanoparticle therein in recent years.

The most regarded method is to prepare an organic-inorganic composite material containing a single inorganic nanoparticle therein by: conjugating several tens of organic ligands having a hydrophilic functional group and a thiol (SH) group to the surface of the nanoparticle through a metal-thiolate (M-S) bond; endowing hydrophilicity to the surface of the nanoparticle by converting the direction of the hydrophilic functional group of the organic ligand outward; and forming a covalent bond between the hydrophilic functional group of the nanoparticle and a biopolymer (see FIG. 2). Such covalent bond may be achieved through the formation of an amide bond or an ester bond between the hydrophilic functional groups of the nanoparticle and the biopolymer. For this, several organic ligands having one of the hydrophilic functional groups such as amine ($NH_2$), carboxylic acid (COOH) or hydroxyl (OH) and a thiol group have been proposed. Such organic ligand can form a M-S bond with numerous nanoparticles such as a semiconductor nanoparticle (e.g., CdSe, ZnS or core/shell CdSe, CdS, CdSe/ZnS), a metal nanoparticle (e.g., Au, Ag) or a metal oxide nanoparticle (e.g., $Fe_2O_3$, $Fe_3O_4$) having metal-rich surface. Among them, since the carboxyl group exhibits high dispersability and solution stability, it has been widely used as a hydrophilic terminal group for conjugating a biopolymer to a nanoparticle by means of an amide bond.

However, said method has to undergo a step for activating the carboxyl group present on the surface of the nanoparticle in a weakly acidic aqueous solution, which results in aggregation and precipitation of many nanoparticles (W C Chan and S Nie, Science 281: 1998; and Jiang et al., *Chem. Mater.* 18: 872, 2006). Thus, precipitated nanoparticles cannot form an amide bond with other molecules due to their significantly reduced dispersibility. Further, another drawback is that a large quantity of nanoparticles is lost during the procedure of removing the precipitated nanoparticles and separating a supernatant containing a small amount of dispersed nanoparticles. Also, the hydroxyl terminal group has to form an ester bond in a strong acid solution or a strong base solution, which also causes the rapid aggregation and precipitation of nanoparticles.

In case that the hydrophilic terminal group is an amine group, it is possible to form an amide bond in a neutral aqueous solution, although it still suffers from the aggregation and precipitation of nanoparticles. In fact, when the aggregated nanoparticles are used as they are, the formation of an amide bond with a biopolymer is carried out only on the surface of the aggregate, which results in the occurrence of poor conversion yield and significantly low quantum efficiency.

To overcome such aggregation and precipitation problems, a method of preparing an organic-inorganic composite material having a M-S bond by reacting a hydrophobic inorganic nanoparticle with poly(ethylene glycol) (PEG) having a thiol terminal group has been suggested (see U.S. Pat. No. 7,041, 371). However, since a long chain of hydrophilic thiol group has to penetrate into the surface of the nanoparticle surrounded with a surfactant even though the conversion yield is partially improved, numerous problems may still arise in that its conversion yield is still low and it does not fundamentally prevent the aggregation of nanoparticles.

Therefore, the present inventors have endeavored to overcome the prior art problems of aggregation and precipitation of hydrophilic nanoparticles having an amine terminal group on the surface thereof, and established a condition for dissociating hydrophilic nanoparticles dispersed in the form of an aggregate in an aqueous solution into a single nanoparticle and individually dispersing them. The organic-inorganic composite material prepared by covalently binding biopolymers to the nanoparticle individually dispersed according to said condition contains only a single inorganic nanoparticle without causing any aggregation or precipitation, thereby exhibiting improved properties such as excellent homogeneity, dispersibility, stability, biocompatibility and targetability.

SUMMARY OF THE INVENTION

Accordingly, the primary object of the present invention is to provide a method of preparing a high quality organic-inorganic composite material, which produces large quantity and high conversion yield, by preventing the nanoparticles from aggregating and precipitating.

It is another object of the present invention to provide an organic-inorganic composite material useful for bioimaging or film coating by using the method of the present invention, which shows excellent dispersibility, prolonged stability and high quantum efficiency.

According to one aspect of the present invention, there is provided a method of preparing an organic-inorganic composite material containing a single inorganic nanoparticle therein, which comprises the steps of:

1) preparing hydrophilic nanoparticles by conjugating organic substances having a thiol group and a hydrophilic amine group to the surface of a core or a core/shell inorganic nanoparticle protected with a surfactant through a metal-thiolate (M-S) bond between them;

2) adjusting the concentration of the hydrophilic nanoparticles prepared in step 1) to $2 \times 10^{-6}$ M or less and treating them in a sonication bath to prepare individually dispersed nanoparticles in the form of a single particle; and 3) conjugating biopolymers to the nanoparticle individually dispersed in step 2) through the formation of an amide bond between them under treatment in a sonication bath.

BRIEF DESCRIPTION OF DRAWINGS

The above and other objects and features of the instant invention will become apparent from the following description of preferred embodiments taken in conjunction with the accompanying drawings, in which.

a) CdSe/CdS-AET nanoparticle prepared in Example 1 b) CdSe/CdS-AET-PEG5000 organic-inorganic composite material prepared in Example 2 c) CdSe/CdS-AET-PEG1900 organic-inorganic composite material prepared in Example 3 d) FA-en-PEG biocompatible-targeting molecule prepared in Example 4 e) CdSe/CdS-AET-PEG-en-FA organic-inorganic composite material prepared in Example 5 f) CdSe/CdS(-AET-PEG-en-FA)(-AET-PEG1900) organic-inorganic composite material prepared in Example 6

Figure 4:
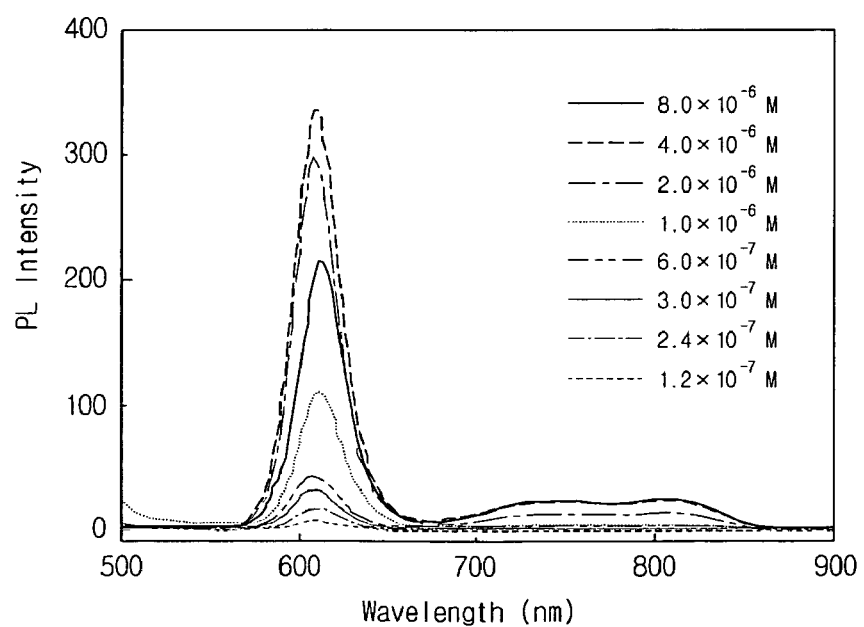
Figure 5:
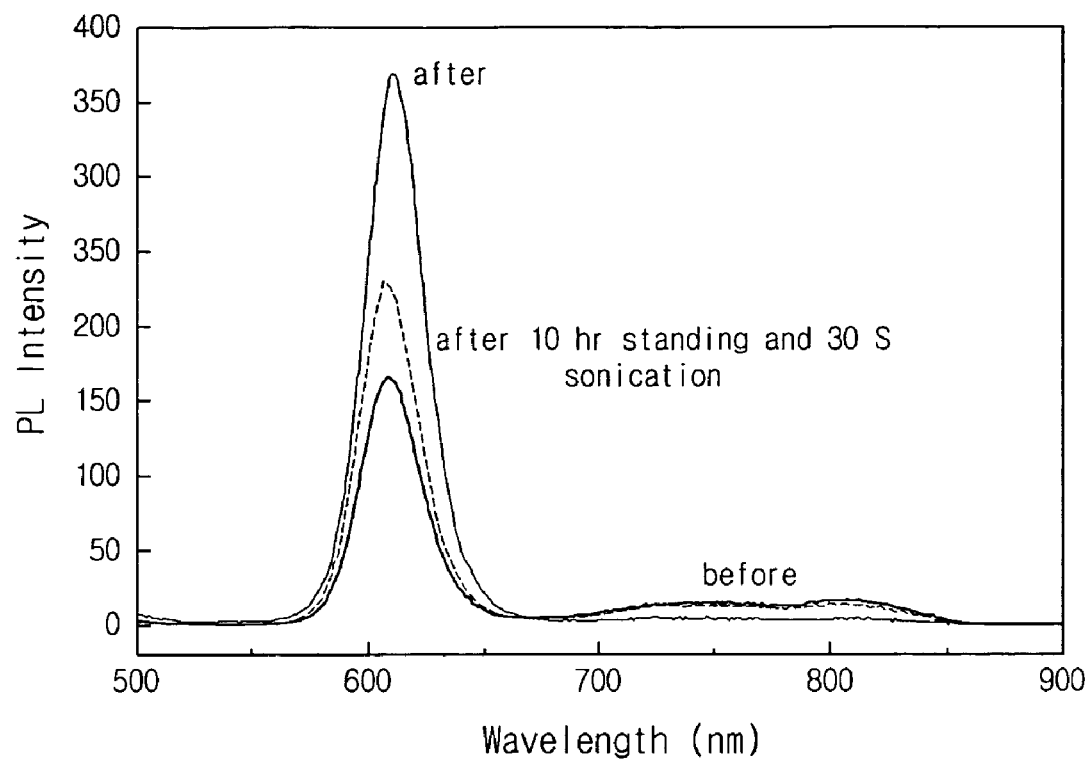
Figure 6:
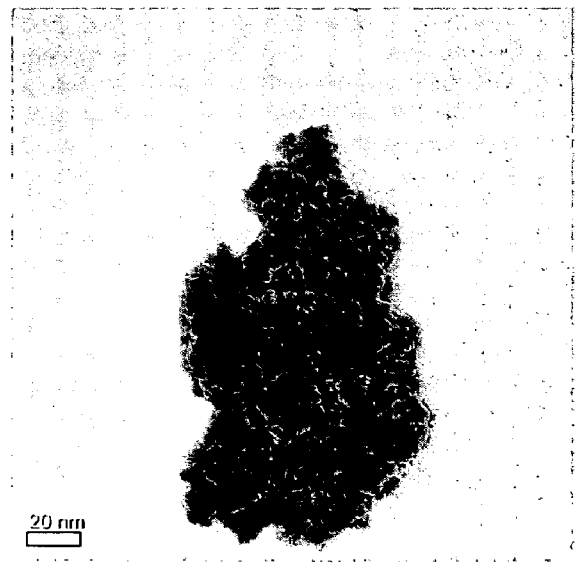
Figure 7:
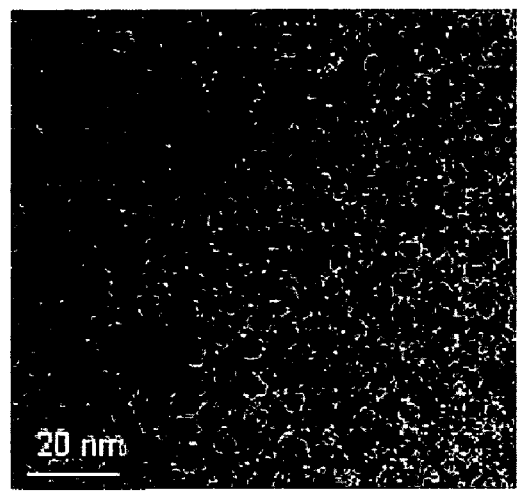
Figure 8:
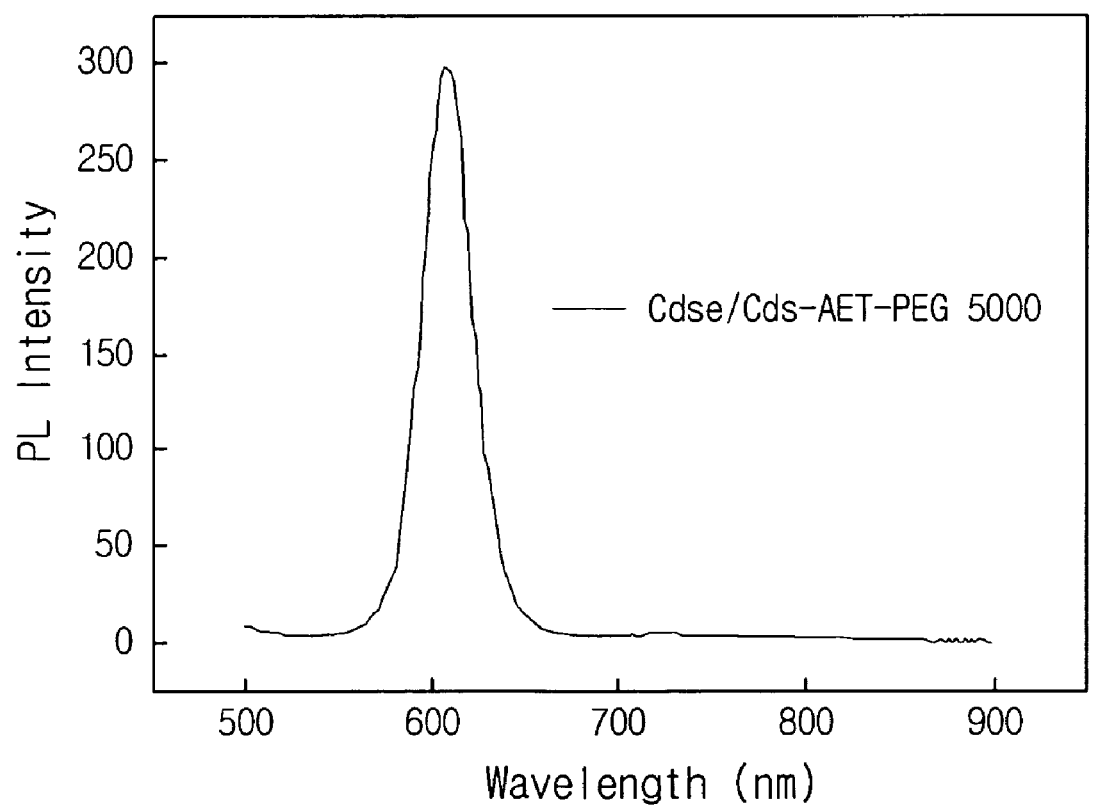
Figure 9:
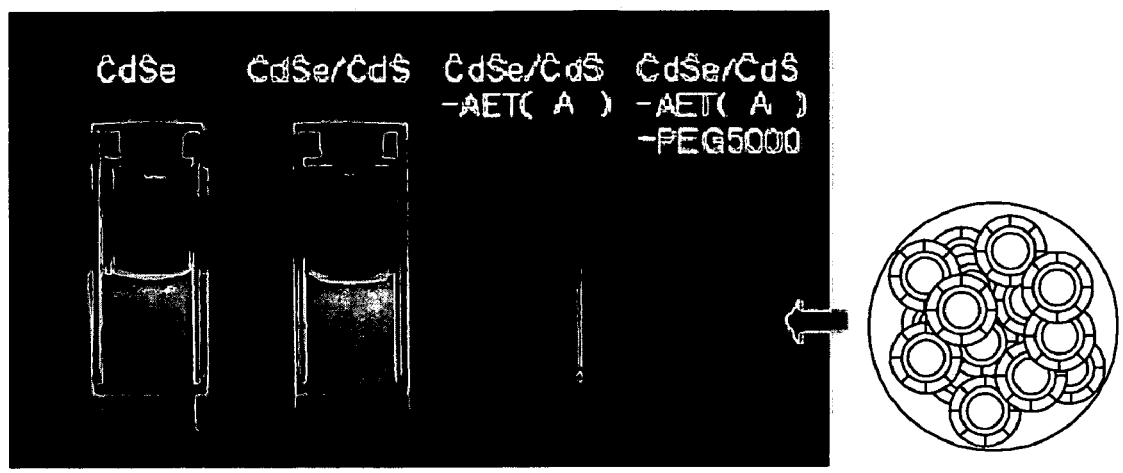
Figure 10:
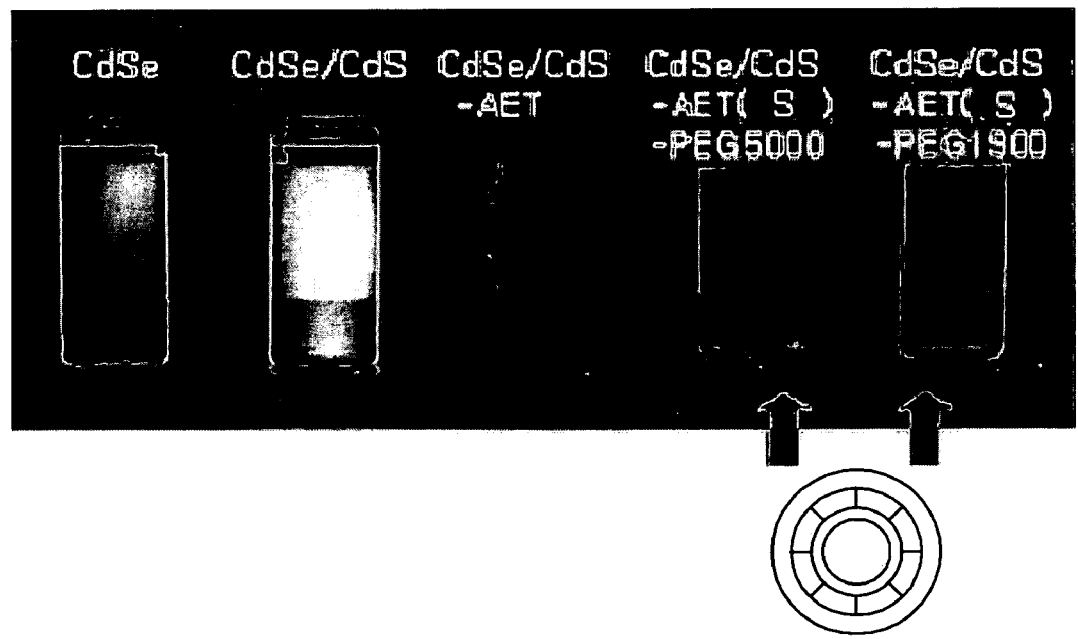
Figure 11:
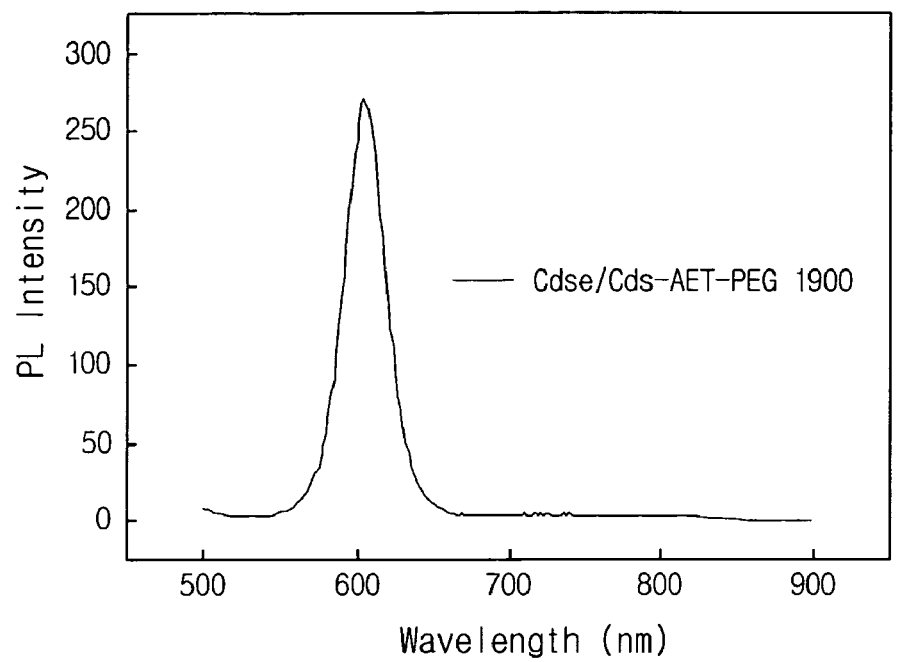
Figure 12:
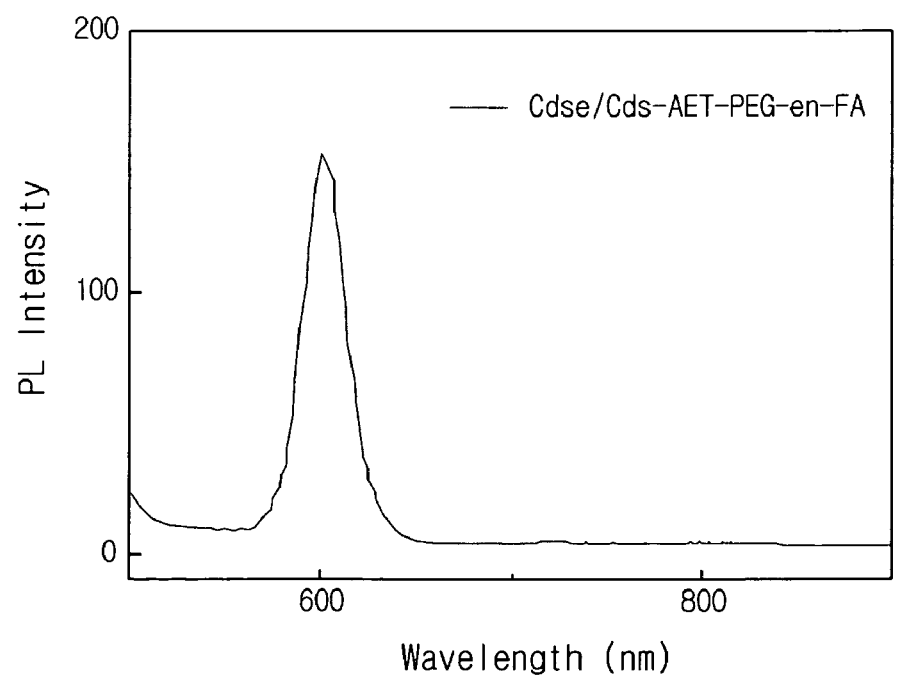
Figure 13:
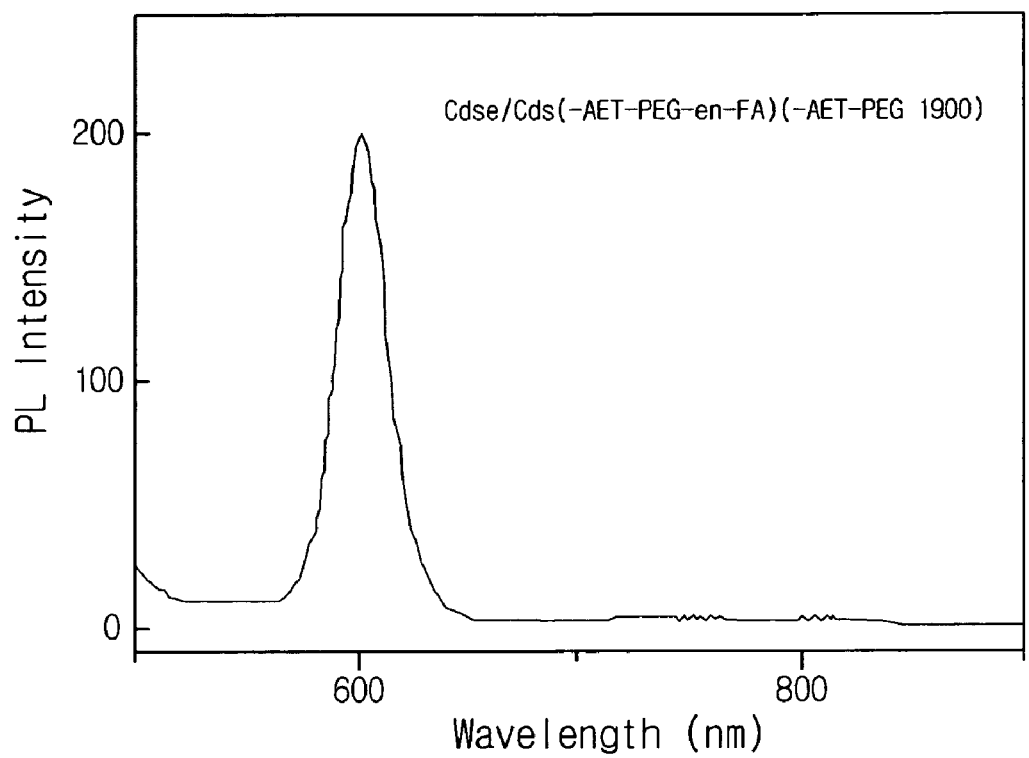
Figure 14:
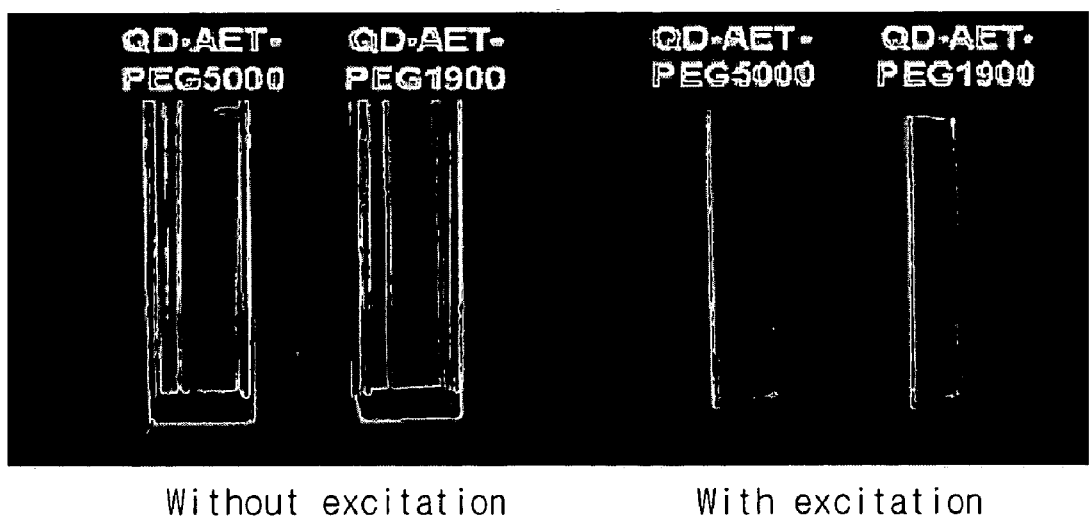

FIG. 4 illustrates photoluminescence spectra of CdSe/CdS-AET nanoparticle prepared in Example 1 in terms of concentration variance;

FIG. 5 illustrates photoluminescence spectra of CdSe/CdS-AET nanoparticles prepared in Example 1 before sonication (a), after sonication (b), and after sonication followed by standing for 10 hours and retreating in a sonication bath (c);

FIG. 6 illustrates a TEM (transmission electron microscope) image of CdSe/CdS-AET nanoparticle prepared in Example 1;

FIG. 7 illustrates a TEM image of CdSe/CdS-AET-PEG5000 organic-inorganic composite material prepared in Example 2;

FIG. 8 illustrates a photoluminescence spectrum of CdSe/CdS-AET-PEG5000 organic-inorganic composite material prepared in Example 2;

FIG. 9 is a photograph of CdSe/CdS-AET(A)-PEG5000 organic-inorganic composite material prepared in Example 2 as a control (A: aggregate) under excitation at 365 nm;

FIG. 10 is a photograph of CdSe/CdS-AET nanoparticle, CdSe/CdS-AET-PEG5000 organic-inorganic composite material and CdSe/CdS-AET-PEG1900 organic-inorganic composite material prepared in Examples 1 to 3, respectively, under excitation at 365 nm;

FIG. 11 illustrates a photoluminescence spectrum of CdSe/CdS-AET-PEG1900 organic-inorganic composite material prepared in Example 3;

FIG. 12 illustrates a photoluminescence spectrum of CdSe/CdS-AET-PEG-en-FA organic-inorganic composite material prepared in Example 5;

FIG. 13 illustrates a photoluminescence spectrum of CdSe/CdS(-AET-PEG-en-FA)(-AET-PEG1900) organic-inorganic composite material prepared in Example 6; and FIG. 14 is a photograph of glass plates coated with CdSe/CdS-AET-PEG5000 and CdSe/CdS-AET-PEG1900 organic-inorganic composite material prepared in Examples 2 and 3, respectively.

DETAILED DESCRIPTION OF THE PREFERRED EMBODIMENTS

The present invention provides a method of preparing an organic-inorganic composite material containing a single inorganic nanoparticle therein, which comprises the steps of:

1) preparing hydrophilic nanoparticles by conjugating organic substances having a thiol group and a hydrophilic amine group to the surface of a core or a core/shell inorganic nanoparticle protected with a surfactant through a metal-thiolate (M-S) bond between them;

2) adjusting the concentration of the hydrophilic nanoparticles prepared in step 1) to $2 \times 10^{-6}$ M or less and treating them in a sonication bath to prepare individually dispersed nanoparticles in the form of a single particle; and 3) conjugating biopolymers to the nanoparticle individually dispersed in step 2) through the formation of an amide bond between them under treatment in a sonication bath.

As described in the prior art, when homogeneous hydrophobic nanoparticles are synthesized in an organic solvent containing a surfactant and an organic ligands having a thiol group and an amine group are conjugated to the surface of the nanoparticle through the formation of a M-S bond, the amine group becomes exposed outward, thereby endowing hydrophilicity to the surface of the nanoparticle. However, in the present invention, since the hydrophilic nanoparticles having the outwardly exposed amine groups strongly tend to aggregate and precipitate, they cannot successfully participate in the formation of an amide bond with the biopolymers. As such, there has not yet been any report for preparing an organic-inorganic composite material containing a single nanoparticle therein, which produces high conversion yield.

The present invention discovered that the hydrophilic nanoparticles having the outwardly exposed amine groups are easy to form an aggregate due to the inter-particle interaction (hydrogen bond) of several tens of hydrophilic functional groups present on the surface thereof, which falls into precipitation. In order to prevent such aggregation and precipitation of nanoparticles, the present invention has established a specific condition for individually dispersing nanoparticles in the form of a single particle in an aqueous solution, rather than collectively dispersing in the form of an aggregate by controlling the concentration and a dispersion method of the nanoparticles for interrupting the inter-particle interaction between them. Since the hydrophilic nanoparticles individually dispersed under said condition successively conduct a conjugation reaction with biopolymers through the formation of an amide bond, it is possible to prepare an organic-inorganic composite material containing a single nanoparticle therein, which shows improved dispersibility and stability.

Figure 1:
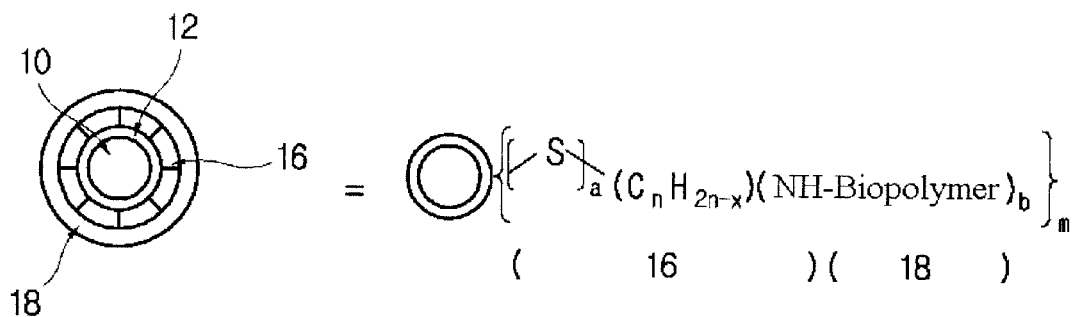
FIG. 1 illustrates a structure of an organic-inorganic composite material containing a single inorganic nanoparticle prepared according to the present invention.
Figure 2:
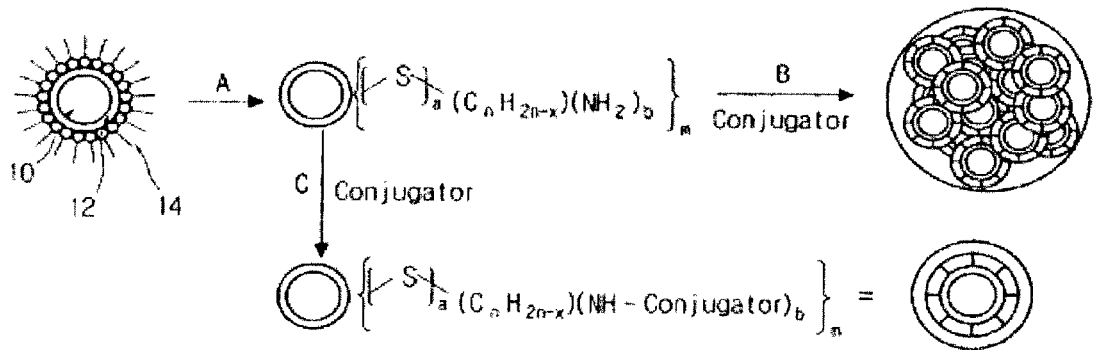
FIG. 2 is a diagram schematically illustrating the preparation procedure of an organic-inorganic composite material according to the present invention.

FIGS. 1 and 2 show the method of preparing an organic-inorganic composite material containing a single nanoparticle therein, which is described in detail below.

In step 1), hydrophobic nanoparticles are subjected to hydrophilic surface modification (see A of FIG. 2), which is carried out by adding an organic substance 16 having a thiol group and an amine group capable of forming a chemical bond with metallic elements present on the surface of a nanoparticle to an organic solution containing a core 10 or a core/shell 12 inorganic nanoparticles protected with a surfactant 14 and reacting the mixture under strong vortexing. This results in the formation of an M-S covalent bond between the metallic element on the surface of the nanoparticle and the thiol group of the organic substance.

The inorganic nanoparticle used in step 1) has a core or a core/shell structure in which the metallic elements are abundant in the surface of the quantum dot (rather than its inside) and are capable of chemically conjugating to the thiol group of the organic substance via an M-S covalent bond. There is no particular limitation as to the type of inorganic nanoparticle used so long as it contains abundant metallic elements on the surface. Preferred examples thereof may include a semiconductor nanoparticle, a metal nanoparticle or a metal oxide nanoparticle. For example, the semiconductor nanoparticle is to be composed of one of the family II elements in a periodic table such as zinc, cadmium and lead and one of the family II elements in a periodic table such as sulfur, selenium and tellurium; the metal nanoparticle, composed of one of Au, Ag, Fe, Co, Ni and Cu; and the metal oxide nanoparticle, composed of iron oxide ($Fe_2O_3$, $Fe_3O_4$). More preferably, the inorganic nanoparticles may be exemplified by CdSe, ZnS, CdSe/CdS, CdSe/ZnS, Au, Ag, $Fe_2O_3$, $Fe_2O_3$ and the like, and further include all nanoparticles composed of a material capable of forming a covalent bond with a thiol group.

The organic substance coupling to the inorganic nanoparticle contains one or two thiol groups and one or two hydrophilic amine groups. Thus, it can form one or two M-S bonds with the inorganic nanoparticle and provide one or two binding sites for coupling with a biopolymer 18 such as a biocompatible molecule, a targeting molecule, a complex thereof (biocompatible-targeting molecule) or a mixture thereof. The particular examples of the organic substance may include an organic substance represented by the following Formula 1:

$$(HS)_a(C_nH_{2n-x})(NH_2)_b \qquad \text{[Formula 1]}$$

wherein $C_nH_{2n-x}$ is a linear or a branched hydrocarbon in which n is an integer in the range of 1 to 20;

a and b are independently 1 or 2;

if both a and b are 1, then x is 0; if a is 1 and b is 2 or a is 2 and b is 1, then x is 1; if both a and b are 2, then x is 2.

The number of organic molecules capable of chemically coupling to the inorganic nanoparticle via an M-S covalent bond between the metallic elements of the inorganic nanoparticle and the thiol groups of the organic substance ranges from 1 to 100. The particular examples of the organic substance may include 2-aminoethanethiol.

The surface modified inorganic nanoparticles prepared in step 1) exhibit hydrophilicity due to the outwardly exposed amine groups, thereby improving dispersibility in water and providing a functional group capable of participating in the following reaction such as conjugation with a biopolymer.

In step 2), the hydrophilic nanoparticles prepared in step 1) is made into a solution having a concentration of $2 \times 10^{-6}$ M or less and treated in a sonication bath so as to interrupt the formation of an aggregate due to an inter-particle interaction, thereby preparing dispersion containing optically and individually dispersed nanoparticles. Since the dispersibility in water of the hydrophilic nanoparticles prepared in step 1) is temporary, they commonly begin to aggregate and precipitate 24 hours after the preparation. Even before 24 hours, if the freshly prepared nanoparticles in the form of an individually dispersed single particle are statically kept for a certain period of time, then the nanoparticles fall into aggregating. Such a phenomenon can be detected as broad trap state emission. Further, in case of forming a relatively small aggregate, its precipitation cannot be observed sometimes. Also, once the nanoparticle aggregate is individually dispersed in the form of a single particle and aggregated again, the reformed aggregate exhibits a stronger cohesive force than before and still represents the broad trap state emission, although it is treated in a sonication bath at a low concentration. This suggests that it is impossible to repeatedly obtain individually dispersed nanoparticles.

Thus, in order to prevent such phenomenon, the present invention employs the hydrophilic nanoparticles within 10 hours after the preparation, preferably immediately after the preparation in the following step. Further, the hydrophilic nanoparticles are maintained at a concentration of $2 \times 10^{-6}$ M or less and treated in a sonication bath, thereby keeping them under the condition of being free from stereoscopically aggregated particulates. As a result of analyzing photoluminescence spectra of the hydrophilic nanoparticles in terms of concentration variance, although the high concentration of the hydrophilic nanoparticle solution does not occur any precipitation, it exhibits a broad and weak trap state emission band at the longer wavelength than the band edge emission of the individually dispersed nanoparticle due to an aggregate formation of hydrophilic nanoparticles, wherein said band edge emission represents a significantly low fluorescent strength (see FIG. 4). However, when the hydrophilic nanoparticle solution adjusts its concentration to $2 \times 10^{-6}$ M or less and reacted with biopolymers, while being treated in a sonication bath according to the present invention, the aggregate formation of the hydrophilic nanoparticles is broken up and the hydrophilic nanoparticle in the form of a single particle is capable of conjugating to the biopolymers. This obtains an organic-inorganic composite material containing a single nanoparticle, which does not show any broad trap state emission and exhibits 5-fold or more increased band edge emission intensity than the previous hydrophilic nanoparticle. Therefore, to prepare an organic-inorganic composite material containing a single nanoparticle, it is very important to employ the individually dispersed hydrophilic nanoparticles immediately after the preparation and maintain their concentration to $2 \times 10^{-6}$ M or less.

Further, it is preferable to perform the treatment in a sonication bath at 50 to 60 Hz for 30 seconds or less.

In step 3), the biopolymers are conjugated to the surface of the hydrophilic nanoparticle (see C of FIG. 2), which may be achieved by forming an amide bond between the individually dispersed nanoparticle and the biopolymer under the treatment in a sonication bath, thereby preparing an organic-inorganic composite material containing a single nanoparticle therein.

The biopolymer used in the present invention refers to a synthetic polymer or a bioconstituent, which is biocompatible and nontoxic. It exhibits various physical properties such as a liquid, a gel or a membrane depending on the biodegradability and environmental conditions, and contains an aldehyde group or an activated carboxyl group at least at one terminal end. The particular examples of the biopolymer may include a biocompatible molecule, a targeting molecule, a complex thereof and a mixture thereof.

It is preferable that the biocompatible molecule is a molecule having an aldehyde group or an activated carboxyl group at both terminal ends or having an aldehyde group or an activated carboxyl group at one terminal end and a $C_{1-10}$ alkoxy group or a hydroxyl group at the other terminal end. The particular examples of the biocompatible molecule may include polyethylene glycol (PEG), dextran, poly(L-lactide) (PLLA), poly(DL-lactide) (PDLLA), poly-DL-lactide/glycolide copolymer (PLGA), chitosan, alginic acid, hyaluronic acid, collagen, heparin, poly(ε-caprolactone) and the like.

Further, the targeting molecule is a molecule, which is specifically recognized in vivo. It is preferable that the targeting molecule has one of an amine group, a hydroxyl group and a thiol group. Thus, it is capable of coupling to the biocompatible molecule through the formation of one of an amide bond, an ester bond and a thioester bond. The targeting molecule useful for the present invention may include: folic acid or methotrexate (MTX) selectively responsible for a folic acid receptor protein; a peptide specific for a certain cell such as RGD peptide or Tat peptide; or an antibody selectively responsible for a specific antigen such as biotin for streptavidin or PSA antibody for PSA.

Further, a biocompatible-targeting molecule prepared in the form of a complex by coupling the biocompatible molecule to the targeting molecule via an amide bond or an ester bond, or a mixture of the biocompatible molecule and the targeting molecule, may be employed.

Since the biopolymer such as a biocompatible molecule, a targeting molecule, a biocompatible-targeting molecule or a mixture thereof has an aldehyde group or an activated carboxyl group at least at one terminal end thereof, it can form an amide bond with an amine group of the hydrophilic nanoparticle individually dispersed in step 2), thereby preparing an organic-inorganic composite material. At this time, in order to maintain individual dispersibility of the hydrophilic nanoparticle, it is preferable to perform the amide formation reaction under treatment in a sonication bath.

Compared to the method of the present invention, as shown in step B of FIG. 2, the prior art method conducts the amide formation reaction of the hydrophilic nanoparticles in the form of an aggregate with the biopolymers. In such a case, since the amide bond may be formed only on the surface of the aggregate, as the nanoparticles existing at interior part of the aggregate cannot contact the biopolymers, they cannot participate in the formation of an amide bond. As a result, several problems occur such as low conversion yield and poor quantum efficiency. Contrast to the above, as described in step C of FIG. 2, since the present invention conducts the amide bond formation reaction under the condition that the hydrophilic nanoparticles are maintained in the form of a single particle by individually dispersing them at a proper concentration with treatment in a sonication bath, several tens of amide bonds can be formed between the single hydrophilic nanoparticle and the biopolymers. Through these procedures, the present invention can prepare an organic-inorganic composite material containing a single nanoparticle therein with a conversion yield of 100% and enhance the quantum efficiency thereof by 4-fold or more.

In a preferred embodiment of the present invention, core or core/shell nanoparticles are synthesized in an organic solution so as to secure homogeneity of the particle, and subjected to surface modification to convert its hydrophobic surface property into hydrophilicity. Thus, the prepared hydrophilic nanoparticle is a spherical particle having a diameter of 10 nm or less and shows fluorescent property. The hydrophilic nanoparticles then adjust their concentration to a proper range and treated in a sonication bath to obtain the individually dispersed hydrophilic nanoparticles in terms of spectroscopic property, which do not show any broad trap state emission band. The hydrophilic nanoparticle thus individually dispersed is conjugated with a biocompatible molecule, a targeting molecule, a biocompatible-targeting molecule or a mixture thereof via an amide bond, thereby preparing an organic-inorganic composite material containing a single nanoparticle therein with a conversion yield of 100%. The organic-inorganic composite material prepared according to the method of the present invention exhibits a part or whole hydrophilicity, biocompatibility and targetability.

Further, in the method of the present invention, as long as the metallic elements present on the surface of the nanoparticle can form a covalent bond with the organic substances having a thiol group regardless of constituent components of an inner inorganic nanoparticle, the nanoparticle can conjugate to biopolymers by means of the amine group of the organic substance. Therefore, the method of the present invention can be effectively applied for the preparation of various types of organic-inorganic composite materials containing a single nanoparticle.

In addition, according to the method of the present invention, although the covalent bond between the inner inorganic nanoparticle and the hydrophilic organic substance is not a M-S bond, if the amine (alkyl amine) groups on the hydrophilic nanoparticle are exposed outward, then it is possible to form an amide bond between the biopolymer and the amine group of the organic substance through the procedures of controlling the concentration of the nanoparticle and treatment in a sonication bath. Thus, it can be effectively applied for the preparation of various organic-inorganic composite materials containing a single nanoparticle. A representative example of hydrophilic nanoparticle without M-S bond can be prepared by conjugating trialkoxy aminopropyl silan to the surface of a silica inorganic nanoparticle.

Further, the present invention provides an organic-inorganic composite material containing a single nanoparticle therein, which is prepared according to the method of the present invention.

The organic-inorganic composite material of the present invention has a structure in which a single hydrophilic nanoparticle including organic substances conjugated to a core or a core/shell inorganic nanoparticle is located at the center and biopolymers are conjugated to hydrophilic amine groups of the hydrophilic nanoparticle via an amide bond.

The organic-inorganic composite material of the present invention does not show any loss of hydrophilic quantum dots due to the aggregation of nanoparticles. Further, since numerous organic ligands exist on the surface of the organic-inorganic composite material and numerous biopolymers can conjugate to the organic ligands, the organic-inorganic composite material of the present invention shows high efficient photoluminescence and photostability as well as excellent chemical stability, dispersibility in water, biocompatibility and targetibility.

Therefore, the organic-inorganic composite material of the present invention can be effectively used as a raw material not only for bioimaging or film coating, but also for diagnosis and treatment of diseases.

The present invention will now be described in detail with reference to the following examples, which are not intended to limit the scope of the present invention.

A core/shell hydrophobic nanoparticle used as a starting material in the following examples is prepared by alternately growing each 0.5 layer of Cd, S, Cd, S and Cd on the surface of a CdSe core nanoparticle according to the method described in the literatures (J J Li et al., *Journal of the Ameri-* can *Chemical Society* 125: 12567-12575, 2003; and W W Yu et al., *Chemistry of Materials* 15: 2854-2869, 2003). However, it is obvious to a person skilled in the art that although the core/shell hydrophobic nanoparticle is prepared by a different method, it can be equally applied to Examples 1 to 6 so long as it is a hydrophobic nanoparticle having metal-rich surface.

EXAMPLE 1

Preparation of Hydrophilic Semiconductor Nanoparticle CdSe/CdS-AET 5 ml of a hydrophobic CdSe/CdS (2.5 layers) quantum dot solution ($2 \times 10^{-5}$ M) was dispersed in 25 ml of chloroform, a methanol solution containing 0.05 M of $HSCH_2CH_2NH_2 \cdot HCl$ (Across, 98%, AET.HCl) was added thereto, and the mixture was vigorously stirred, yielding precipitation. When the precipitation does not occur any further, distilled water was added to the resulting mixture, thereby transferring CdSe/CdS-AET modified its hydrophobic surface into hydrophilic to an aqueous layer (upper layer). There was no precipitation or photoluminescence in the chloroform layer, which means that there was no loss of quantum dots.

The aqueous layer taken therefrom was mixed with a solvent mixture of methanol and ethyl acetate to induce precipitation and then subjected to centrifugation to separate a precipitate. The separated precipitate was washed with the solvent mixture of ethanol and ethyl acetate and dispersed in distilled water, thereby preparing a CdSe/CdS-AET solution in which CdSe/CdS-AET nanoparticles are stabilized by means of a Cd—S bond and exhibit hydrophilicity due to outwardly exposed amine groups.

Figure 3:
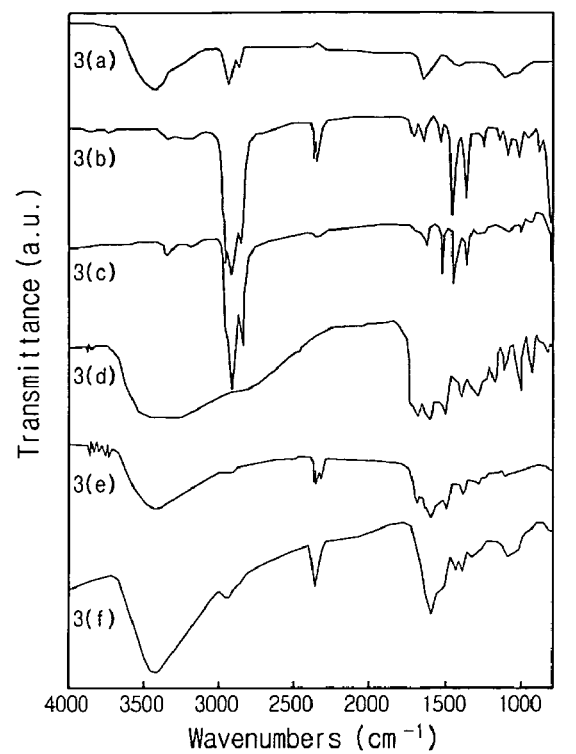
FIG. 3 illustrates IR spectra of composite materials prepared in Examples 1 to 5.

The hydrophilic CdSe/CdS-AET nanoparticles synthesized above were analyzed with IR and photoluminescence spectra in terms of concentration variance and the results are shown in (a) of FIG. 3 and FIG. 4. The IR spectrum confirmed that AET was conjugated to the surface of a quantum dot and the photoluminescence spectrum proved that the lower the concentration of the nanoparticles is, the weaker the intensity of broad trap state emission band around 700 to 850 nm is. Further, FIG. 5 shows photoluminescence spectra of CdSe/CdS-AET nanoparticles ($2 \times 10^{-6}$ M) before sonication, after sonication for 30 seconds, and after sonication followed by standing for 10 hours and re-treating in a sonication bath for 30 seconds. This suggests that when the hydrophilic nanoparticles are treated in a sonication bath immediately after the preparation, the broad trap state emission band around 700 to 850 nm disappears. However, once the hydrophilic nanoparticle solution was in stand for a certain period of time, even if it was repeatedly treated in a sonication bath, the broad trap state emission band was still detected. These results suggest that the quantum dot aggregate in a solution state can be dissolved and individually dispersed only at the initial stage of the preparation procedure. Further, the fact that the broad trap state emission band disappears and the band edge emission is only detected demonstrated that the quantum dot solution was converted into an organic-inorganic composite material containing a single nanoparticle. FIG. 6 illustrates a TEM image of CdSe/CdS-AET nanoparticles, which shows that the nanoparticles fall into an aggregate as the solvent is gradually evaporated on a TEM grid.

EXAMPLE 2

Preparation of Organic-Inorganic Composite Material CdSe/CdS-AET-PEG5000

10 ml of CdSe/CdS-AET nanoparticle solution prepared in Example 1 adjusted its concentration to $2 \times 10^{-6}$ M and treated in a sonication bath. After sonication, it was observed that there was no broad trap state emission around 700 to 850 nm range. After 0.02 g of poly(ethylene glycol) monomethyl ether mono(succinimidyl succinate) ester (PEG5000, Polyscience Inc., Mw=5000) (200 equivalents) was dissolved in 2 ml of acetonitrile, it was added to the diluted nanoparticle solution. The resulting mixture was treated in a sonication bath and stirred alternately and repeatedly for 6 hours. It was further stirred for 12 hours. A solvent mixture of methanol and ethyl acetate was added thereto to thereby obtain a precipitate. The precipitate was separated by centrifugation, washed with methanol five times and then dispersed in dichloromethane. There was no fluorescent light in a supernatant removed after centrifugation, which suggests a full conversion of nanoparticles into a composite material (100% conversion yield).

IR spectrum, TEM image and photoluminescence spectrum of the CdSe/CdS-AET-PEG5000 organic-inorganic composite material prepared above are shown in (b) of FIG. 3, FIG. 7 and FIG. 8, respectively. IR spectrum demonstrated that PEG5000 was successfully conjugated to the surface of the nanoparticle, while TEM image showed that each quantum dot existed separately and there was no aggregation. These results confirmed that the CdSe/CdS-AET-PEG5000 organic-inorganic composite material contains only a single quantum dot therein. Further, it has been confirmed by the photoluminescence spectrum that the broad trap state emission around 700 to 850 nm range disappears and the quantum efficiency of the organic-inorganic composite material was increased by 5-fold (8.3%) higher than CdSe/CdS-AET (1.7%) nanoparticle.

To compare with this, after the CdSe/CdS-AET nanoparticle solution was prepared according to the same method as described in Example 1, 4 ml of a sample ($5 \times 10^{-6}$ M) showing the broad trap state emission around 700 to 850 nm range was taken therefrom 1 day after the preparation and then diluted by 2.5-fold with distilled water. 0.020 g of PEG5000(200 eq) was dissolved in 2 ml of acetonitrile, added to the diluted sample and stirred for a day. The resulting solution was mixed with methanol and ethyl acetate to thereby obtain a precipitate. The precipitate was washed with methanol five times or more. The resulting precipitate was dispersed in distilled water. At this time, fluorescent light was still detected in the waste solution removed after centrifugation in the washing step, which means that the conversion reaction is not efficiently performed. Further, it has been found that thus obtained organic-inorganic composite material showed 0.1% or below quantum efficiency and exhibited extremely weak fluorescent light. A real image obtained by exciting the aggregated quantum dot solution prepared as a control with a light source of 365 nm is shown in FIG. 9, and a diagram schematically illustrating the theoretical structure thereof was represented together therewith. In FIG. 9, the reason why fluorescent light of the organic-inorganic composite material was insignificant was that although the nanoparticles were dispersed, their amide bond formation reaction with PEG was conducted only at the surface of hydrophilic CdSe/CdS-AET nanoparticle, which still existed in the form of an aggregate, thus resulting in significantly lowering conversion yield and quantum efficiency.

EXAMPLE 3

Preparation of Organic-Inorganic Composite Material CdSe/CdS-AET-PEG1900

Some of the CdSe/CdS-AET solution prepared in Example 1 was taken, made into 10 ml of a sample at a concentration of $1\times10^{-6}$ M, and treated in a sonication bath. After the treatment in a sonication bath, it was confirmed that the sample did not show any broad trap state emission around 700 to 850 nm range. After 4.8 mg of PEG1900 (Polysciences Inc. Mw=1900, 250 eq) was added thereto, the mixture was sonicated with intermittent vortexing for 6 hours followed by vortexing for 12 hours under dark and inert atmosphere. Methanol and ethyl acetate were added into the reaction mixture to form a precipitate. The precipitate separated by centrifugation was washed with methanol five times or more and dispersed in dichloromethane, thereby obtaining a CdSe/CdS-AET-PEG1900 organic-inorganic composite material solution. There was no fluorescent light around 700 to 850 nm range in the waste solution removed after centrifugation, which means that the reaction yield is 100%.

Real images obtained by exciting the organic-inorganic composite material solutions prepared in Examples 1 to 3 with a light source of 365 nm are shown in FIG. 10. Further, a diagram schematically illustrating the theoretical structure of the organic-inorganic composite material containing a single nanoparticle was represented together therewith. As illustrated in FIG. 10, the organic-inorganic composite materials (CdSe/CdS-AET-PEG5000 and CdSe/CdS-AET-PEG1900) containing a single nanoparticle of Examples 2 and 3 exhibited significantly higher fluorescence intensity than CdSe/CdS-AET nanoparticle of Example 1. FT-IR and photoluminescence spectra of CdSe/CdS-AET-PEG1900 organic-inorganic composite material prepared in Example 3 are shown in (c) of FIG. 3 and FIG. 11, respectively. It was confirmed from the FT-IR spectrum that PEG1900 is successfully conjugated to the surface of the nanoparticle. Further, the photoluminescence spectrum demonstrated that there is no trap state emission evolution around 700 to 850 nm range and its quantum efficiency is about 6-fold (10%) higher than CdSe/CdS-AET (1.7%). These results suggest that the organic-inorganic composite material containing a single nanoparticle therein is successfully prepared in a high conversion yield.

EXAMPLE 4

Preparation of Biocompatible-Targeting Molecule (FA-en-PEG)

441 mg of folic acid (FA, 1 mmol) was dissolved in 14 ml of dimethyl formamide (DMF) and stirred in an ice-cold bath for 10 minutes. 226 mg of dicyclohexyl carbodiimide (DCC, 1.1 mmol) was added and stirred for 18 hours. 2.5 ml of ethylene diamine(en) in 20 ml of DMF was added to the above solution and stirred for 3 hours. Water and acetonitrile were added to form a FA-en precipitate and subjected to recrystallization with the same solvent. In another flask, 1.98 g of polyethylene glycol dicarboxylic acid (PEG600 dicarboxylic acid, Mw=600, 3.3 mmol) was dissolved in 8 ml of DMF and stirred in an ice-cold bath for 10 minutes. 1.572 g of DCC (6.9 mmol) was added and stirred for 18 hours. After the resulting mixture was heated to room temperature, 1.61 mg of the FA-en precipitate (0.33 mmol) was added thereto and stirred at room temperature for 5 hours. The resulting mixture was filtered to remove a white floating solid. Thus obtained filtrate was mixed with a large quantity of diethyl ether to form a precipitate and stored in a cold chamber for 12 hours. Then, the precipitate was separated by filtration, washed with cold diethyl ether and dried under vacuum, thereby obtaining 162 mg of FA-en-PEG. FT-IR spectrum of FA-en-PEG biocompatible-targeting molecule is shown in (d) of FIG. 3.

EXAMPLE 5

Preparation of CdSe/CdS-AET-PEG-en-FA Showing Hydrophilicity, Biocompatibility and Targetability Some of the CdSe/CdS-AET solution prepared in Example 1 was taken, made into 10 ml of a sample at a concentration of $1\times10^{-6}$ M, and treated in a sonication bath. After the treatment in a sonication bath, it was confirmed that the sample did not show any broad trap state emission around 700 to 850 nm range. After 2.8 mg of FA-en-PEG (100 eq) prepared in Example 4 was added to the sample, the mixture was sonicated with intermittent vortexing for 6 hours followed by further stirring for 12 hours. Methanol and ethyl acetate were added into the reaction mixture to form a precipitate. The precipitate separated by centrifugation was washed with methanol/ethyl acetate mixture five times or more. Thus separated precipitate by centrifugation was suspended in distilled water to thereby obtain CdSe/CdS-AET-PEG-en-FA organic-inorganic composite material. FT-IR and photoluminescence spectra of the organic-inorganic composite material prepared above are shown in (e) of FIG. 3 and FIG. 12, respectively. It was confirmed from the FT-IR spectrum that FA-en-PEG is successfully conjugated to the surface of the nanoparticle. Further, the photoluminescence spectrum demonstrated that there is no fluorescence around 700 to 850 nm range and its quantum efficiency is about 4-fold (6.9%) higher than CdSe/CdS-AET (1.7%).

EXAMPLE 6

Preparation of CdSe/CdS (-AET-PEG-en-FA)(-AET-PEG1900) Showing Hydrophilicity, Biocompatibility and Targetability Some of the CdSe/CdS-AET solution prepared in Example 1 was taken, made into 10 ml of a sample at a concentration of $1\times10^{-6}$ M, and treated in a sonication bath. After the treatment in a sonication bath, it was confirmed that the sample did not show any broad trap state emission around 700 to 850 nm range. After 1.12 mg of FA-en-PEG (40 eq) prepared in Example 4 was added to the sample, the mixture was sonicated with intermittent vortexing for 1 hour and succeedingly added 38.5 mg of PEG1900 (200 eq). The resulting mixture was sonicated with intermittent vortexing for 6 hours followed by further stirring for 12 hours. Methanol and ethyl acetate were added into the reaction mixture to form a precipitate. The precipitate separated by centrifugation was washed with methanol/ethyl acetate mixture five times or more. The fact that it takes a significantly long time to induce the precipitation due to high solubility of PEG1900 as compared with CdSe/CdS-AET-PEG-en-FA means that PEG1900 is evenly conjugated to the nanoparticle. The separated solid by centrifugation was suspended in distilled water to thereby obtain CdSe/CdS(-AET-PEG-en-FA)(-AET-PEG1900) organic-inorganic composite material. FT-IR and photoluminescence spectra of the organic-inorganic composite material prepared above are shown in (f) of FIG. 3 and FIG. 13, respectively. It was confirmed from the FT-IR spectrum that the mixture of FA-en-PEG and PEG1900 is successfully conjugated to the quantum dot. Further, the photoluminescence spectrum demonstrated that there is no fluorescence around 700 to 850 nm range and its quantum efficiency is about 4.5-fold (7.6%) higher than CdSe/CdS-AET (1.7%).

EXAMPLE 7

Glass plates were soaked in the organic-inorganic composite material solutions prepared in Examples 2 and 3 several times and dried to prepare the glass plates coated with each organic-inorganic composite material containing a single nanoparticle. Images of the glass plates obtained by exciting with or without a light source of 365 nm are shown in FIG. 14.

As illustrated in FIG. 14, it was found that the organic-inorganic composite material prepared according to the present invention can be effectively used for coating a film.

As apparent form the forgoing, the preparation method of the present invention can prepare an organic-inorganic composite material containing a single nanoparticle therein with a conversion yield of 100% by individually dispersing hydrophilic nanoparticles in the form of a single particle through the concentration control and treatment in a sonication bath and conjugating with a biopolymer such as a biocompatible molecule, a targeting molecule, a biocompatible-targeting molecule or a mixture thereof via an amide bond. Further, in the method of the present invention, as long as metallic elements present on the surface of the nanoparticle can form a covalent bond with organic substances having a thiol group regardless of constituent components of an inner inorganic nanoparticle, the nanoparticle can conjugate to biopolymers by means of the amine group of the organic substance. Therefore, the method of the present invention can be effectively applied for the preparation of various types of organic-inorganic composite materials containing a single nanoparticle. Since the organic-inorganic composite material prepared by the method of the present invention is a spherical particle having a diameter of 10 nm or less and shows high efficient photoluminescence and photostability as well as excellent chemical stability, dispersibility in water, biocompatibility and targetibility, it can be effectively used as a raw material not only for bioimaging or film coating, but also for diagnosis and treatment of diseases.

While the present invention has been described and illustrated with respect to a preferred embodiment of the invention, it will be apparent to those skilled in the art that variations and modifications are possible without deviating from the broad principles and teachings of the present invention, which should be limited solely by the scope of the claims appended hereto.

What is claimed is:

1. A method of preparing an organic-inorganic composite material containing a single nanoparticle therein, comprising the steps of:
   1) preparing hydrophilic nanoparticles by conjugating a surface of a core or core/shell inorganic nanoparticle to an organic substance having a thiol group and a hydrophilic amine group, the surface of the inorganic nanoparticle comprising a metallic element and being protected by a surfactant, said conjugation comprising formation of a metal-thiolate (M-S) bond between the metallic element of the inorganic nanoparticle and the thiol group of the organic substance;
   2) individually dispersing the hydrophilic nanoparticles by diluting the hydrophilic nanoparticles to a concentration of $2 \times 10^{-6}$ M or less within 10 hours after step 1) and treating the diluted hydrophilic nanoparticles in a sonication bath; and
   3) forming an organic-inorganic composite material containing a single nanoparticle therein by conjugating a biopolymer to the individually dispersed nanoparticles, said conjugation comprising formation of amide bonds between the biopolymer and the amine groups of the organic substance during treatment in a sonication bath.

2. The method of claim 1, wherein the inorganic nanoparticle in step 1) comprises a metal nanoparticle comprising one of Au, Ag, Fe, Co, Ni and Cu; a metal oxide nanoparticle comprising iron oxide; or a semiconductor nanoparticle comprising one of zinc, cadmium and lead and one of sulfur, selenium and tellurium.

3. The method of claim 2, wherein the inorganic nanoparticle comprises a material selected from the group consisting of CdSe, ZnS, CdSe/CdS, Au, Ag, $Fe_2O_3$ and $Fe_3O_4$.

4. The method of claim 1, wherein the organic substance in step 1) contains one or two thiol groups and one or two hydrophilic amine groups.

5. The method of claim 4, wherein the organic substance has a structure represented by the following Formula 1:

$$(HS)_a(C_nH_{2n-x})(NH_2)_b \qquad \text{<Formula 1>}$$

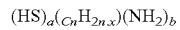

wherein $C_nH_{2n-x}$ is a linear or a branched hydrocarbon, where n is an integer ranging from 1 to 20;
a and b are independently 1 or 2;
if both a and b are 1, x is 0; if a is 1 and b is 2 or a is 2 and b is 1, x is 1; if both a and b are 2, x is 2.

6. The method of claim 4, wherein the organic substance is 2-aminoethanethiol.

7. The method of claim 1, wherein each inorganic nanoparticle forms metal-thiolate (M-S) bonds with from 1 to 100 units of the organic substance.

8. The method of claim 1, wherein the hydrophilic nanoparticles in step 1) comprise outwardly exposed aminoalkyl groups on the surface thereof.

9. The method of claim 1, wherein the treatment in a sonication bath in step (2) is conducted at 50 to 60 Hz for 30 seconds or less.

10. The method of claim 1, wherein the biopolymer comprises a biocompatible molecule, a targeting molecule, a complex thereof or a mixture thereof.

11. The method of claim 10, wherein the biocompatible molecule comprises an aldehyde group at both ends, or comprises an activated carboxyl group at both ends, or comprises an aldehyde group or an activated carboxyl group at one end and a $C_{1-10}$ alkoxy group or a hydroxyl group at another end.

12. The method of claim 11, wherein the biocompatible molecule is selected from the group consisting of polyethylene glycol (PEG), dextran, poly(L-lactide) (PLLA), poly (DL-lactide) (PDLLA), poly-DL-lactide/glycolide copolymer (PLGA), chitosan, alginic acid, hyaluronic acid, collagen, heparin and poly(ε-caprolactone).

13. The method of claim 10, wherein the targeting molecule is a molecule specifically recognized in vivo and includes one of an amine group, a hydroxyl group and a thiol group and is capable of conjugating to the biopolymer through the formation of one of an amide bond, an ester bond or a thioester bond.

14. The method of claim 13, wherein the targeting molecule is folic acid, methotrexate (MTX), a peptide specific for a certain cell or an antibody selectively responsible for a specific antigen.

15. The method of claim 10, wherein the complex is prepared by coupling the biocompatible molecule to the targeting molecule via an amide bond or an ester bond.

* * * * *